US 9,560,988 B2

(12) United States Patent
Carbonera et al.

(10) Patent No.: US 9,560,988 B2
(45) Date of Patent: Feb. 7, 2017

(54) SYSTEM AND METHOD FOR RENDERING AN IMAGE OF AN ELONGATE MEDICAL DEVICE

(75) Inventors: Carlos Carbonera, St. Paul, MN (US); Daniel R. Starks, Lake Elmo, MN (US); Lev A. Koyrakh, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1506 days.

(21) Appl. No.: 12/980,732

(22) Filed: Dec. 29, 2010

(65) Prior Publication Data

US 2012/0172713 A1 Jul. 5, 2012

(51) Int. Cl.
*A61B 5/05* (2006.01)
*A61B 5/06* (2006.01)
*A61B 5/00* (2006.01)

(52) U.S. Cl.
CPC .............. *A61B 5/065* (2013.01); *A61B 5/6855* (2013.01)

(58) Field of Classification Search
USPC ........................ 600/422–424, 431, 433–434
See application file for complete search history.

(56) References Cited

U.S. PATENT DOCUMENTS 6,990,370 B1 * 1/2006 Beatty et al. ................. 600/509
2004/0116775 A1 * 6/2004 Taniguchi et al. ............ 600/117
2008/0221425 A1 * 9/2008 Olson et al. .................. 600/407
2008/0294034 A1 * 11/2008 Krueger et al. .............. 600/409
2010/0168558 A1 * 7/2010 Olson ........................... 600/424

OTHER PUBLICATIONS

Bennink, H.E. et al., "Warping a Neuro-Anatomy Atlas on 3D-MRI Data With Radial Basis Functions," In: Proc. Intern. Conf. on Biomedical Engineering (Biomed), pp. 1-4 (Dec. 2006).
Carr, J.C. et al., "Reconstruction and Representation of 3D Objects With Radial Basis Functions," Annual Conference on Computer Graphics SIGGRAPH, pp. 67-76 (2001).
Liu, Xiaopei et al., "Interactive Image Morphing Using Thin-Plate Spline," ShaderX7 Advanced Rendering Techniques (ed. Wolfgang Engel) Sec. 9.5, pp. 743-752 (2009).
Reinsch, Christian H., "Smoothing by Spline Functions," 13 Numer. Math Bd. 10 pp. 177-183 (1967).

* cited by examiner

*Primary Examiner* — Amanda Lauritzen Moher
*Assistant Examiner* — Shahdeep Mohammed
(74) *Attorney, Agent, or Firm* — Dykema Gossett PLLC

(57) ABSTRACT

A system for visually rendering an elongate medical device in a body is provided. The system includes an electronic control unit configured to find a measured physical location for each of a plurality of position sensors on the elongate medical device. The electronic control unit is further configured to apply a spline function to each of the measured physical locations to determine a display location for each position sensor. The electronic control unit is further configured to interpolate between display locations of adjacent position sensors to identify display locations for portions of the elongate medical device between adjacent position sensors. The electronic control unit is further configured to generate image data for display of an image of the elongate medical device including the display locations of the position sensors and the display locations of the portions of the elongate medical device between adjacent position sensors.

20 Claims, 4 Drawing Sheets

SYSTEM AND METHOD FOR RENDERING AN IMAGE OF AN ELONGATE MEDICAL DEVICE

BACKGROUND OF THE INVENTION a. Field of the Invention

This invention relates to a system for visually rendering a catheter or other elongate medical device in a body. Specifically, the instant invention relates to a system that corrects systematic measurement noise to improve image rendering accuracy.

b. Background Art

Catheters are used to perform a variety of tasks within human bodies and other bodies including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface, among other tasks. In order to properly administer treatment, the position and orientation of a catheter inside the body must be continuously monitored. One known technique for determining the position and orientation of a catheter within a body is by tracking a plurality of sensors on the catheter using a position sensing and navigation system (sometimes called a location mapping system). In one exemplary system offered for sale by St. Jude Medical, Inc. under the trademark "ENSITE NAVX", the sensors comprise electrodes. Excitation of pairs of electrodes on the outer surface of the body generates electrical fields within the body. Voltage measurements on the catheter electrodes can then be used to determine the position and orientation of the catheter electrodes within a coordinate system of the position sensing and navigation system. Other exemplary position sensing and navigation systems include magnetic systems.

In order to provide information to clinicians about the position and orientation of the catheter, the determined position and orientation of the catheter sensors is often used to render an image of the catheter relative to surrounding tissues, including heart tissues. One drawback to conventional systems, however, is that the determined position and orientation of the catheter sensors is subject to systematic errors due to subtle differences in, e.g., sensor impedances and amplifier channels. These errors can distort the rendered shape of the catheter from its true mechanical shape in the resulting image.

The inventors herein have recognized a need for a system for visually rendering a catheter or other elongate medical device in a body that will minimize and/or eliminate one or more of the above-identified deficiencies.

BRIEF SUMMARY OF THE INVENTION

It is desirable to provide a system for visually rendering a catheter or other elongate medical device in a body. Specifically, it is desirable to provide a system that corrects for systematic measurement errors to more accurately render an image of the catheter or other elongate medical device in a body.

A system for visually rendering a catheter or other elongate medical device in accordance with one embodiment of the invention includes an electronic control unit configured to find a measured physical location for each of a plurality of position sensors on the elongate medical device and to apply a spline function to each of the measured physical locations to determine a display location for each position sensor. The electronic control unit is further configured to interpolate between display locations of adjacent position sensors to identify display locations for portions of the elongate medical device between adjacent position sensors. The electronic control unit is further configured to generate image data for display of an image of the elongate medical device including the display locations of the position sensors and the display locations of the portions of the elongate medical device between adjacent position sensors.

A system in accordance with the present invention is advantageous because it allows for correction of systematic measurement noise as well as errors in position and orientation measurements of sensors on the elongate medical device. As a result, the catheter image more accurately reflects the actual position, orientation and shape of the catheter, permitting clinicians to offer more effective diagnosis and treatment.

DETAILED DESCRIPTION OF EMBODIMENTS OF THE INVENTION

Figure 1:
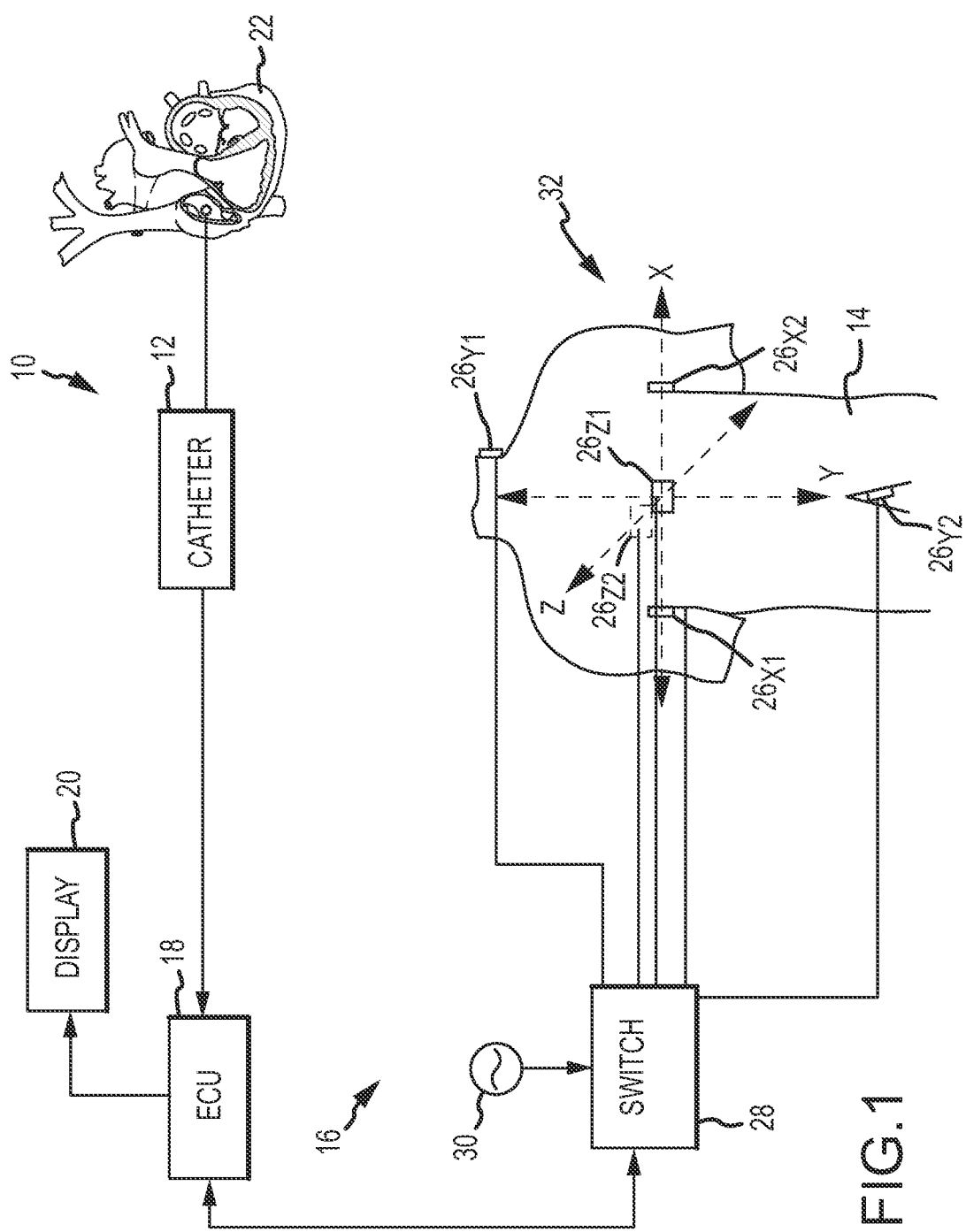
FIG. 1 is a diagrammatic view of a system for visually rendering an elongate medical device in a body in accordance with one embodiment of the present invention.

FIG. 1 illustrates one embodiment of a system 10 in accordance with the present invention for visually rendering an elongate medical device, such as a catheter 12, in a body 14. Although the system is described in terms of rendering a catheter, it should be understood that various elongate medical devices (e.g., introducer sheaths, pacing leads, etc.) could be rendered using the inventive system. System 10 may include a position sensing system 16, an electronic control unit (ECU) 18 and a display 20.

Catheter 12 may comprise an electrophysiological (EP) catheter for use in gathering EP data associated with the heart 22 to enable generation of an image of the geometry of the heart surface and related EP data. Catheter 12 may also allow removal of bodily fluids or injection of fluids and medicine into the body and may further provide a means for transporting surgical tools or instruments within a body including those used for pacing or tissue ablation. Although catheter 12 comprises an EP catheter in the illustrated embodiment, it should be understood that the inventive system can be used to visually render a variety of different types of catheters including, for example, intracardiac echocardiography (ICE) catheters and ablation catheters using a wide variety of ablative energies (e.g., radio-frequency, cryogenic, ultrasound, laser or other light, etc.). Catheter 12 may be formed from conventional materials such as polyurethane. Catheter 12 is tubular and is deformable and may be guided within a body by a guide wire or other means known in the art. Catheter 12 has a proximal end and a distal end. As used herein, "distal" refers to an end of catheter 12 that is advanced to the region of interest within body 14 while "proximal" refers to the opposite end of catheter 12 that is disposed outside of the body 14 and manipulated manually by a clinician or automatically through, for example, robotic controls. Catheter 12 may be inserted within a vessel located near the surface of a body (e.g., in an artery or vein in the leg, neck, or arm) in a conventional manner and maneuvered to a region of interest in body 14 such as heart 22.

Figure 2:
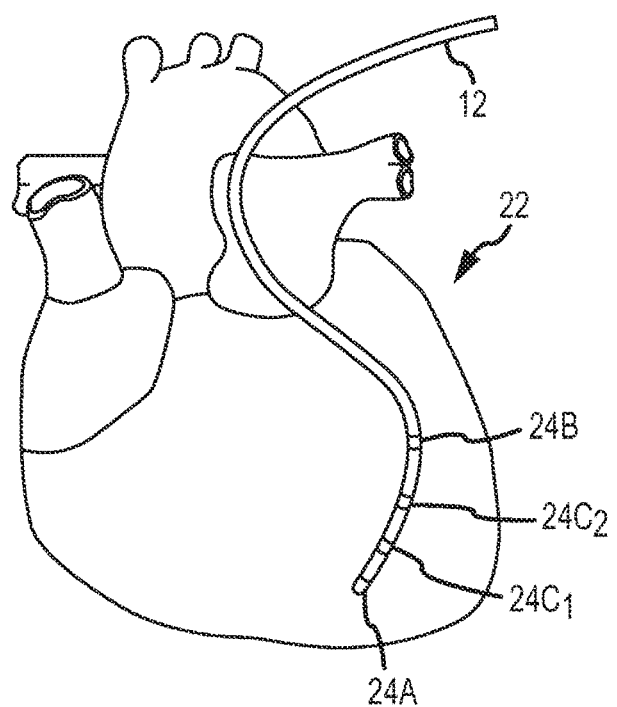
FIG. 2 is a diagrammatic view of the distal end of a catheter within a human heart.

Referring to FIG. 2, catheter 12 may include a plurality of EP mapping electrodes 24 such as distal tip electrode 24A, proximal ring electrode 24B, and intermediate ring electrodes 24C. Electrodes 24 are provided to generate information regarding the position of catheter 12 and therefore may function as position sensors in accordance with the present invention. Electrodes 24 also provide information regarding the geometry of heart 22 and other EP data as discussed in greater detail hereinbelow.

Position sensing system 16 is provided to determine the position and orientation of position sensors such as electrodes 24 on an elongate medical device such as catheter 12. In accordance with one embodiment of the invention, system 16 may include patch electrodes 26, a multiplex switch 28 and a signal generator 30. Patch electrodes 26 are attached to body 14 and are provided to generate electrical signals used in determining the position of catheter 12 within a three dimensional coordinate system 32 and in generating EP data regarding heart 22. Electrodes 26 are placed orthogonally on the surface of body 14 and are used to create axes specific electric fields within body 14. Electrodes $26_{X1}$, $26_{X2}$ may be placed along a first (x) axis. Similarly, electrodes $26_{Y1}$, $26_{Y2}$ may be placed along a second (y) axis and electrodes $26_{Z1}$, $26_{Z2}$ may be placed along a third (z) axis. In addition, a reference electrode (not shown) may also be attached to body 12. Each of the electrodes 26 may be coupled to multiplex switch 28. ECU 18 is configured through appropriate software to provide control signals to switch 28 and thereby sequentially couple pairs of electrodes 26 to a signal generator 28. Excitation of each pair of electrodes 26 generates an electrical field within body 14 and within an area of interest such as heart 22. Voltage levels at non-excited electrodes 26 are filtered and converted and provided to ECU 18 for use as reference values.

The electrodes 24 on catheter 12 are disposed within electrical fields created in body 14 (e.g., within the heart 22) by exciting patch electrodes 26. The electrodes 24 experience voltages that are dependent on the location between the patch electrodes 26 and the position of the electrodes 24 relative to the surface of the heart 22. Voltage measurement comparisons made between electrodes 24 can be used to determine the position of the electrodes 24 within heart 22. Movement of the electrodes 24 within heart 22 (e.g., within a heart chamber) produces information regarding the geometry of the heart 22 as well as EP data.

In the illustrated embodiment, the position sensors on catheter 12 comprise electrodes 24 and position sensing system 16 relies on the generation of electrical fields from a source located outside of body 14. It should be understood, however, that the positions sensors and position sensing system may take on other forms conventional in the art. For example, the position sensors may comprise coils and the position sensing system may rely on the generation of magnetic fields as in the positioning system offered for sale under the trademark "gMPS" by Mediguide, Ltd. Further, the position sensors on catheter 12 may act as the source of an electrical or magnetic field with corresponding electrodes or coils outside of body 14 generating position and orientation information based on detection of the generated field.

Electronic control unit (ECU) 18 provides a means for controlling the operation of various components of system 10 including catheter 12 and switch 28. Where catheter 12 comprises an EP catheter, ECU 18 also provides a means for determining the geometry of heart 14 and EP characteristics of heart 14. ECU 18 further provides a means for determining the position and orientation of catheter 12 and for generating display signals used to control display 20. ECU 18 may comprise a programmable microprocessor or microcontroller or may comprise an application specific integrated circuit (ASIC). ECU 18 may include a central processing unit (CPU) and an input/output (I/O) interface through which ECU 18 may receive a plurality of input signals including signals generated by patch electrodes 26 and catheter 12 (particularly position sensors on catheter 12 such as electrodes 24) and generate a plurality of output signals including those used to control and/or provide data to catheter 12, display 20, and switch 28.

Figure 3:
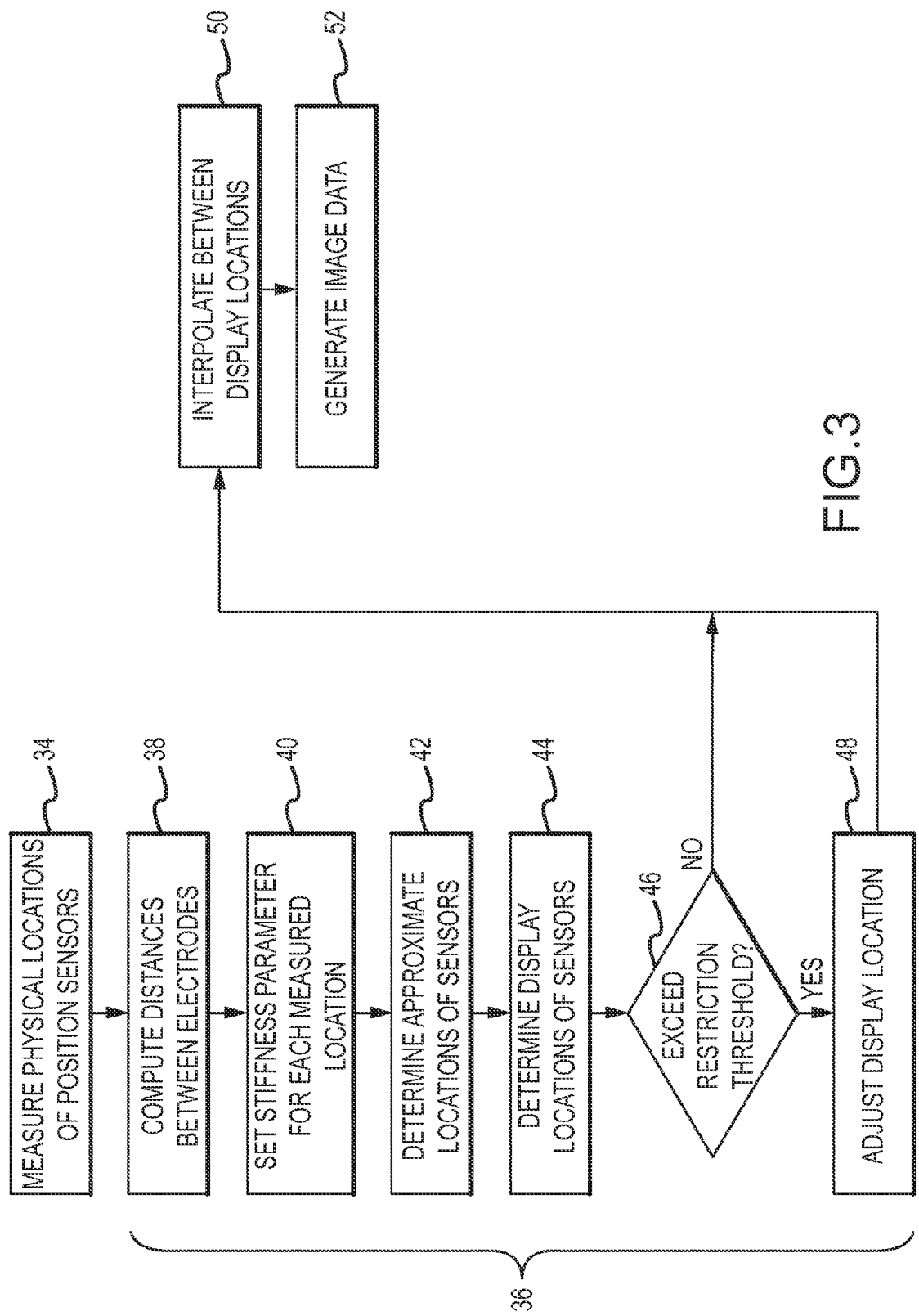
FIG. 3 is a flow chart illustrating a method for visually rendering an elongate medical device in a body in accordance with one embodiment of the present invention.

Referring to FIG. 3, a method for visually rendering an elongate medical device, such as catheter 12, in body 14 is illustrated. The method may be implemented in ECU 18 through the use of programming instructions or code (i.e., software) that configures ECU 18 to perform the steps of the method. The method may begin with the step 34 of finding a measured physical location for each of a plurality of position sensors on the elongate medical device within body 14 such as electrodes 24 on catheter 12. In operation, ECU 18 may—in the illustrated embodiment—generate signals to control switch 28 and thereby selectively energize patch electrodes 26. ECU 18 receives position signals from electrodes 24 on catheter 12 reflecting changes in voltage levels on electrodes 24 and from the non-energized patch electrodes 26. ECU 18 uses the raw location data produced by electrodes 24, 26 and corrects the data to account for respiration and other artifacts.

Because of systematic measurement noise due to subtle differences in, e.g., sensor impedances and amplifier channels, the position of an electrode 24 within coordinate system 32 calculated from raw voltage measurement comparisons may be different from the true physical location of electrode 24 within coordinate system 32. Therefore, an image of the catheter 12 generated from the raw voltage measurement comparisons may be distorted from the true shape and position of catheter 12. The inventive system corrects for this distortion to render a more visually accurate depiction of elongate medical devices such as catheter 12.

In accordance with the invention, the method may continue with the step 36 of applying a spline function to each of the measured physical locations to determine a display location for each position sensor. In one embodiment of the invention, the spline function comprises a thin plate spline function and step 36 may include several substeps 38, 40, 42, 44, 46, 48.

In substep 38, the Pythagorean distance in three-dimensional space from each electrode to the neighboring electrode is computed (i.e., 24A to $24C_1$, $24C_1$ to $24C_2$, etc.). From these measurements, the total distance of each electrode from the first (most distal) electrode on the catheter, measured down the length of the catheter, is computed by summing the Pythagorean distances. For example, for a catheter with N electrodes at respective coordinates $\{x_i, y_i, z_i\}$, the distances u would be computed as:

$$u_1 = 0$$

$$u_2 = \sqrt{(x_2-x_1)^2+(y_2-y_1)^2+(z_2-z_1)^2}$$

$$u_3 = u_2 + \sqrt{(x_3-x_2)^2+(y_3-y_2)^2+(z_3-z_2)^2}$$

$$u_N = u_{N-1} + \sqrt{(x_N-x_{N-1})^2+(y_N-y_{N-1})^2+(z_N-z_{N-1})^2}$$

The measured distances are used to determine the approximate location of each sensor as described hereinbelow.

In substep 40, a stiffness parameter (designated) is set for each measured physical location to control the degree to which the display locations can be shifted from their measured physical locations. In one embodiment of the invention, for example, the stiffness parameter for the measured physical locations for one or both of distal electrode 24A and proximal electrode 24B is set to zero such that the display locations are not shifted from the measured physical locations for electrodes 24A and/or 24B and the display locations will be the same as the measured physical locations. The stiffness parameters for the measured physical locations of other electrodes such as electrodes 24C is set to non-zero values to permit a predetermined degree of shift in position.

In substep 42, an approximate location for each position sensor is determined responsive to measured coordinates of the position sensor along each of the three coordinate axes. Towards this end, three independent sets of thin plate spline equations are solved—one set of equations for each coordinate axis. The number of the thin plate spline equations in each set is equal to the number of electrodes 24 on the catheter or other elongated medical device. For each coordinate axis, the distances $u_i$ determined at step 38 and the measured coordinates from step 34 can be treated as pairs of reference points that may be used to define a spline. Referring to an exemplary catheter with three electrodes, for the x-axis, the pairs are $\{u_1, x_1\}$, $\{u_2, x_2\}$, $\{u_3, x_3\}$; for the y-axis, $\{u_1, y_1\}$, $\{u_2, y_2\}$, $\{u_3, y_3\}$; for the z-axis, $\{u_1, z_1\}$, $\{u_2, z_2\}$, $\{u_3, z_3\}$. In each coordinate plane (i.e. UX, UY, UZ), a line can be drawn extending through corresponding reference pairs. In each plane, the algorithm for computing that line may be the same. In each plane the line is the linear combination of N radial basis functions $\psi_i(u)$. In one embodiment, cubic functions may be used as radial basis functions:

$$\psi_i(u) = |u-u_i|^3$$

each with the center at the corresponding $u_i$. In further embodiments, other basis functions may also be used with the algorithm.

The smoothing parameter chosen in step 40 ($\lambda_i$) may be integrated into a linear combination of radial basis functions and linear functions computed at reference points $u_j$, which must be equal to the corresponding $x_i$:

$$x_i = b^x u_j + c^x + \sum_{j=1}^{N} a_j^x (\psi(u_i - u_j) - \lambda \delta_{ij})$$

$$\sum_{j=1}^{N} a_j^x = 0$$

$$\sum_{j=1}^{N} a_j^x u_j = 0$$

where $\delta_{ij}$ are Kornecker symbols defined by the following equations:

$$\delta_{ij}=1, i=j$$

$$\delta_{ij}=0, i \neq j.$$

If the sensors at the ends of the catheter are required to be rendered at exactly measured locations, then rather than standard Kornecker symbols, the generalized Kornecker symbols could be used, defined by the following equations:

$$\delta_{ij}=1, i=j, i \neq 1, N,$$

$$\delta_{ij}=0, i \neq j, i=1, N.$$

Similarly, setting the value of the smoothing parameter $\lambda_i$ to zero for any sensor will result in that sensor being rendered at exactly the measured location.

Solving the combination for unknown numbers $a_j^x$, $b^x$, and $c^x$ yields a spline function for determining the approximate x-coordinate for each of N sensors on the catheter:

$$x(u) = b^x u + c^x + \sum_{j=1}^{N} a_j^x \psi(u - u_j)$$

Similar combinations can be solved to yield similar spline functions for determining the approximate y- and z-coordinates for each of N sensors on the catheter:

$$y(u) = b^y u + c^y + \sum_{j=1}^{N} a_j^y \psi(u - u_j)$$

$$z(u) = b^z u + c^z + \sum_{j=1}^{N} a_j^z \psi(u - u_j)$$

At step 44, a display location in three-dimensional space for each electrode 24 may be determined by combining the output of the functions from step 42. Thus, the display location for a particular sensor i is $\{x(u_i), y(u_i), z(u_i)\}$. Alternatively, for an electrode with smoothing parameter $\lambda_i$ set to zero, the measured physical location may be used as the display location.

In accordance with one embodiment of the invention, the difference in value between the measured physical location and the determined display location is restricted. Accordingly, in substep 46 the measured physical location and the display location for each position sensor is compared. If the difference between the measured physical location and the computed display location for each position sensor exceeds a threshold value, the display location is adjusted at substep 48 so that the display location is disposed at a point along a vector connecting the measured physical location and previously computed display location and the point differs from the measured physical location by no more than the threshold value.

The method may continue with the step 50 of interpolating between display locations of adjacent position sensors such as electrodes 24 to identify display locations for those portions of the catheter 12 or other elongate medical device between adjacent position sensors. The display locations for these portions of catheter 12 may be determined using a cubic spline interpolation in accordance with one embodiment of the invention.

The method may conclude with the step 52 of generating image data for display of an image of the catheter 12 or other elongate medical device including the determined display locations for the electrodes 24 or other position sensors and the display location of the portions of the catheter 12 or other device between the electrodes 24 or other position sensors. ECU 18 may generate the image data and provide it to display 20.

Display 20 is provided to convey information to a clinician to assist in diagnosis and treatment. Display 20 may comprise a conventional computer monitor or other display device. Display 20 presents a graphical user interface (GUI) to the clinician. The GUI may include a variety of information including, for example, an image of the geometry of heart 22, EP data associated with heart 22, graphs illustrating voltage levels over time for various electrodes, and images of catheter 22 and electrodes 24.

Figure 4A:
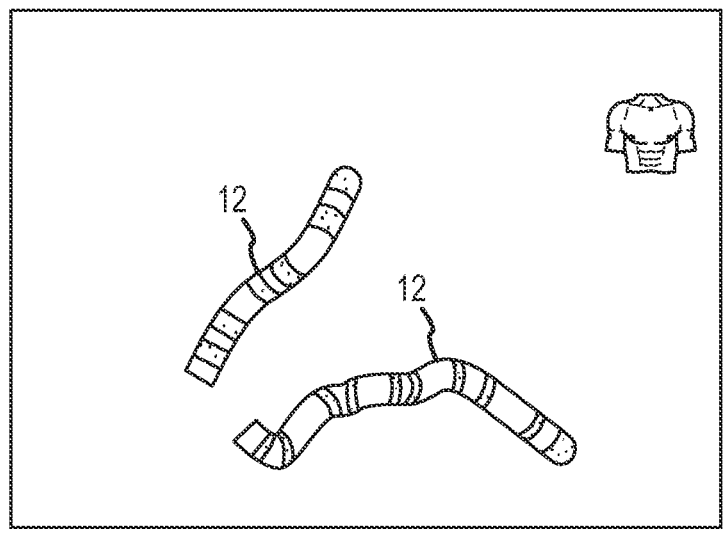
FIGS. 4A and 4B are display screens illustrating the rendered image of a catheter using a prior art system and a system in accordance with the present invention, respectively.
Figure 4B:
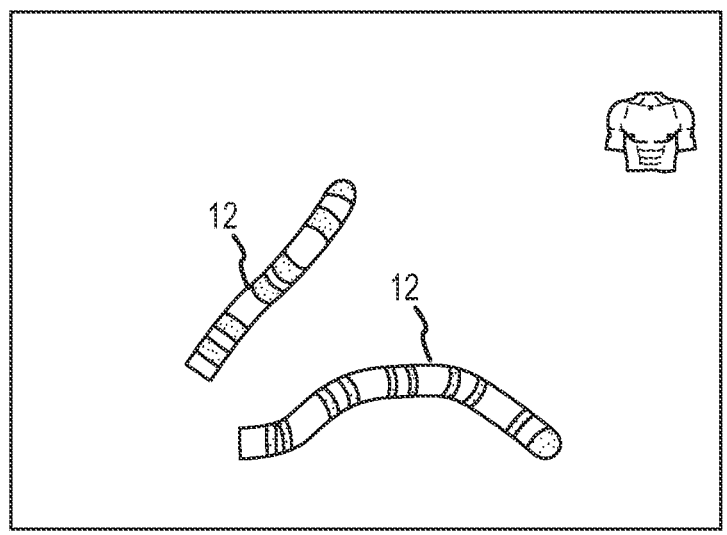

Referring to FIGS. 4A and 4B, images from a display illustrating multiple catheters 12 are shown using conventional rendering techniques (FIG. 4A) and the inventive system and method (FIG. 4B). As illustrated in FIGS. 4A and 4B, the inventive system is advantageous relative to conventional systems because it allows for correction of systematic measurement noise as well as errors in position and orientation measurements of sensors on the elongate medical device that distort the natural shape and actual position of the catheter. As a result, an image of the catheter 12 rendered using the inventive system more accurately reflects the actual position, orientation and shape of the catheter 12, permitting clinicians to offer more effective diagnosis and treatment.

Although several embodiments of this invention have been described above with a certain degree of particularity, those skilled in the art could make numerous alterations to the disclosed embodiments without departing from the scope of this invention. For example, different thin plate spline basis functions could be used in the invention and splines other than cubic splines could be used to determined display locations for the position sensors. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for visually rendering an elongate medical device in a body, said device having a distal and a proximal end, comprising:
    an electronic control unit comprising a central processing unit and an input/output interface configured to receive signals generated by a plurality of position sensors on said elongate medical device and to output said image data to a display, said electronic control unit configured to:
        find a measured physical location for each of said plurality of position sensors on said elongate medical device within said body;
        compute and apply a spline function to each of said measured physical locations to determine a display location for each position sensor;
        interpolate between display locations of adjacent position sensors to identify display locations for portions of said elongate medical device between said adjacent position sensors; and,
        generate image data for display of an image of said elongate medical device including said display locations of said position sensors and said display locations of said portions of said elongate medical device between said adjacent position sensors.

2. The system of claim 1 wherein said spline function is a thin plate spline function.

3. The system of claim 1 wherein said electronic control unit is further configured, in computing and applying said spline function, to determine a first approximate location for a first position sensor of said plurality of position sensors responsive to a first set of coordinates for said plurality of position sensors along a first coordinate axis and a second approximate location for said first position sensor responsive to a second set of coordinates for said plurality of position sensors along a second coordinate axis.

4. The system of claim 3 wherein said display location for a first position sensor is determined responsive to said first approximate location and said second approximate location of said first position sensor.

5. The system of claim 1 wherein said electronic control unit is further configured, in computing and applying said spline function, to determine a distance from a distal position sensor of said plurality of position sensors to each of the other position sensors of said plurality of position sensors.

6. The system of claim 1 wherein said display location of a first position sensor of said plurality of position sensors is said measured physical location of said first position sensor.

7. The system of claim 6 wherein said first position sensor is located nearer said distal end of said device than any other position sensor of said plurality of position sensors.

8. The system of claim 6 wherein said first position sensor is located nearer said proximal end of said device than any other position sensor of said plurality of position sensors.

9. The system of claim 1 wherein a distance between the display location of a first position sensor of said plurality of position sensors and the measured physical location of said first position sensor is restricted by a value such that said distance is less than or equal to said value.

10. The system of claim 1 wherein said display locations for portions of said elongate medical device between said adjacent position sensors are determined using a cubic spline interpolation.

11. A system for visually rendering an elongate medical device in a body, said device having a distal and a proximal end, comprising:
    a position sensing system disposed outside of said body and configured to interact with a plurality of position sensors on said elongate medical device upon generation of at least one of an electric field and a magnetic field;
    an electronic control unit comprising a central processing unit and an input/output interface configured to receive signals generated by said plurality of position sensors on said elongate medical device and to output said image data to a display, said electronic control unit configured to:
        find a measured physical location for each of said plurality of position sensors responsive to signals generated by at least one of said position sensor and said position sensing system;

compute and apply a spline function to each of said measured physical locations to determine a display location for each position sensor;

interpolate between display locations of adjacent position sensors to identify display locations for portions of said elongate medical device between said adjacent position sensors; and, generate image data for display of an image of said elongate medical device including said display locations of said position sensors and said display locations of said portions of said elongate medical device between said adjacent position sensors.

12. The system of claim 11 wherein said spline function is a thin plate spline function.

13. The system of claim 11 wherein said electronic control unit is further configured, in computing and applying said spline function, to determine a first approximate location for a first position sensor of said plurality of position sensors responsive to a first set of coordinates for said plurality of position sensors along a first coordinate axis and a second approximate location for said first position sensor responsive to a second set of coordinates for said plurality of position sensors along a second coordinate axis.

14. The system of claim 13 wherein said display location for a first position sensor is determined responsive to said first approximate location and said second approximate location of said first position sensor.

15. The system of claim 11 wherein said electronic control unit is further configured, in computing and applying said spline function to determine a distance from a distal position sensor of said plurality of position sensors to each of the other position sensors of said plurality of position sensors.

16. The system of claim 11 wherein said display location of a first position sensor of said plurality of position sensors is said measured physical location of said first position sensor.

17. The system of claim 16 wherein said first position sensor is located nearer said distal end of said device than any other position sensor of said plurality of position sensors.

18. The system of claim 16 wherein said first position sensor is located nearer said proximal end of said device than any other position sensor of said plurality of position sensors.

19. The system of claim 11 wherein a distance between the display location of a first position sensor of said plurality of position sensors and the measured physical location of said first position sensor is restricted by a value such that said distance is less than or equal to said value.

20. The system of claim 11 wherein said display locations for portions of said elongate medical device between said adjacent position sensors are determined using a cubic spline interpolation.

* * * * *